Figure 1:
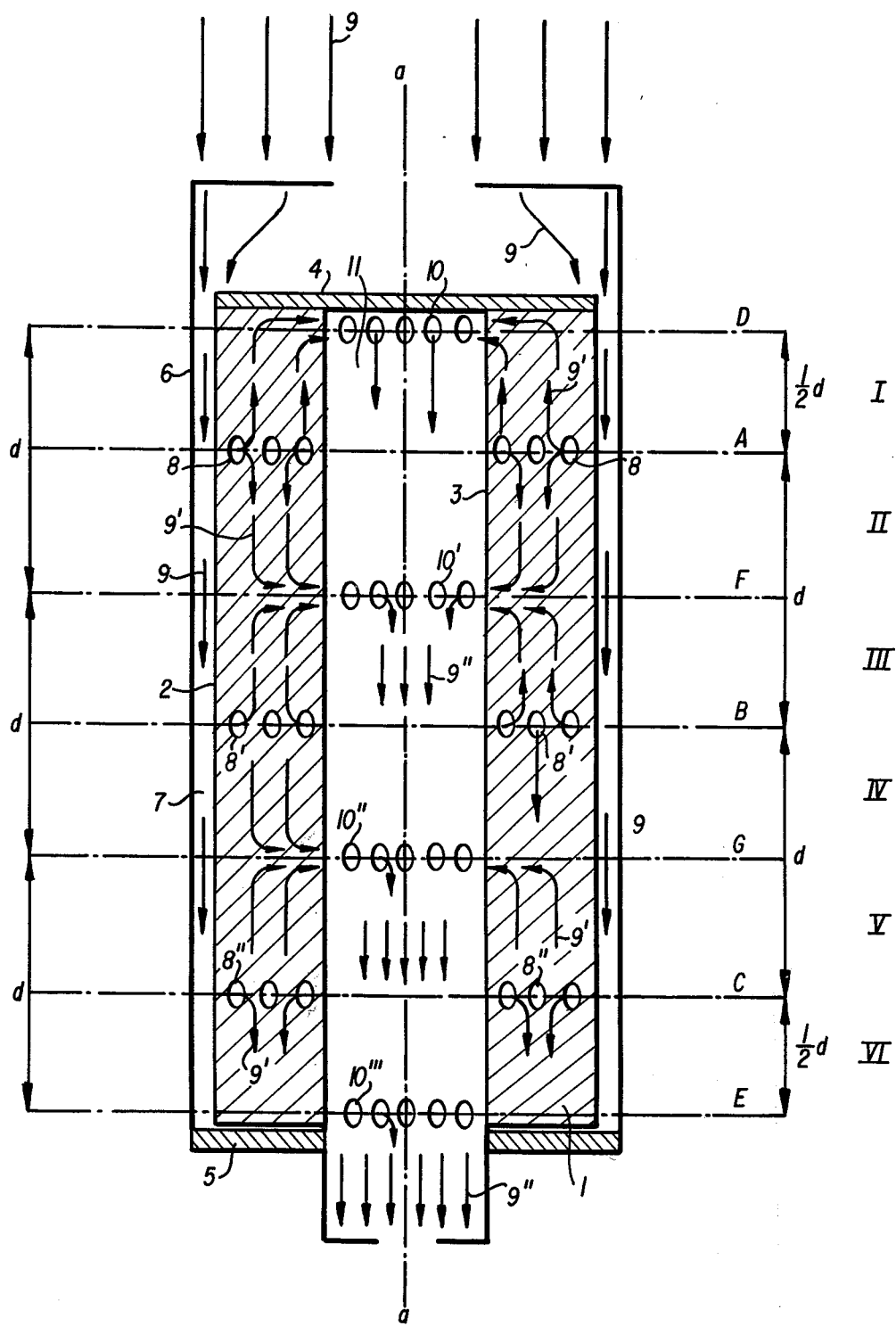

United States Patent [19]

Gramatica

[11] 4,205,044

[45] May 27, 1980

[54] REACTOR FOR CATALYZED EXOTHERMIC REACTIONS

[75] Inventor: Giorgio Gramatica, Milan, Italy

[73] Assignee: Tecnimont S.p.A., Milan, Italy

[21] Appl. No.: 835,005

[22] Filed: Sep. 20, 1977

[30] Foreign Application Priority Data

Sep. 24, 1976 [IT] Italy .............................. 27626 A/76

[51] Int. Cl.² .............................................. B01J 8/04
[52] U.S. Cl. .................... 422/191; 422/192; 422/194; 422/203; 422/207; 422/208; 422/218; 422/148
[58] Field of Search ................. 23/288 R, 288 K, 289; 423/360, 361; 422/148, 191, 192, 193, 194, 218, 203, 207, 208

[56] References Cited

U.S. PATENT DOCUMENTS

| | | | |
|---|---|---|---|
| 2,234,169 | 3/1941 | Houdry ............................ | 23/288 R |
| 3,372,988 | 3/1968 | Hansen ............................ | 423/360 X |
| 3,433,609 | 3/1969 | Percival et al. ................. | 23/288 R X |
| 3,751,232 | 8/1973 | Borre ................................ | 23/288 R |
| 3,753,662 | 8/1973 | Pagani ............................. | 23/289 |
| 3,754,078 | 8/1973 | Hinrich et al. .................. | 23/289 X |
| 3,941,869 | 3/1976 | Fuchs .............................. | 23/288 R X |
| 3,996,014 | 12/1976 | Müller et al. ................... | 23/288 R |

*Primary Examiner*—Michael S. Marcus
*Attorney, Agent, or Firm*—Stevens, Davis, Miller & Mosher

[57] ABSTRACT

A catalytic reactor for catalyzed exothermic reactions is disclosed having at least one catalyst layer, characterized in that each individual layer is arranged between two coaxial cylindrical shells, at least two inlets for the reacting gases to the catalyst being provided in one of said shells and at least two outlets in the other shell. The inlets are provided in the external cylindrical shell, and the outlets are provided in the internal cylindrical shell. The inlets and outlets consist of a plurality of openings made in said cylindrical shells and aligned on circumferences that are intersections of the cylindrical shells with equidistant planes perpendicular to the axis of said cylindrical shells.

1 Claim, 2 Drawing Figures

REACTOR FOR CATALYZED EXOTHERMIC REACTIONS

This invention relates to a reactor for catalyzed exothermic reactions such as, for example, the synthesis of ammonia or methanol.

For such reactions, which are generally conducted under a high pressure, it is already known to arrange the catalytic mass in two or more layers through which the reacting gases are made to flow, an intermediate cooling of said gases being provided between each layer and the successive one in order to keep the catalyst temperature in a defined range and to increase the conversion yield.

The layers of catalyst generally lie one upon the other, are contained in a vertical cylindrical shell, and are arranged to be traversed by the reacting gases while flowing in axial direction, and generally downwardly.

The main drawback of this type of reactor is the considerable pressure drop occurring in each catalyst layer, which compels one to progressively increase the reactor diameter as the desired production capacity increases, this involving an increase in the reactor weight and cost. Furthermore, beyond a certain production capacity, one would exceed the size limitations imposed by the present technological capabilites of the pressure vessel manufacturers and of the means of transportation from the site of manufacture to the point of use.

It is also well known that, with a view to obviating such drawbacks, catalytic reactors have been suggested in which the catalyst was arranged to be traversed by the reacting gases flowing in a radial direction or a direction perpendicular to the axis of the cylindrical shell containing the catalyst. The utilization of such types of reactor, though it permits one to reduce the pressure drops of the reacting gases flowing through the catalytic mass, nevertheless creates considerable problems concerning the uniform distribution of the reacting gases in the catalytic mass, since the section of said catalytic mass—that is, perpendicular to the direction of flow of the reacting gases—varies continuously. This fact compels one to resort to special devices for the distribution of the reacting gases, these devices however being expensive and requiring much space.

Another type of reactor has also been suggested in which the various catalyst layers are grouped in a single mass contained in a cylindrical shell, the flow of reacting gases being divided into two streams that enter the catalytic mass from its opposite ends, i.e., from the top and from the bottom, and flow through said catalytic mass in an axial direction and in opposite directions until converging to an outlet located in an intermediate position in respect of the two ends of the catalytic mass, which requires that the catalyst mass shall be substantially split nto two symmetrical parts lying one over the other.

Such a type of reactor presents the drawback of involving a doubling of the devices for the intermediate cooling of the reacting gases. This represents a complication in the construction of the reactor and presents serious problems in case one should decide to effect said intermediate cooling by heat removal with the generation of water vapor. With such a reactor type, moreover, the pressure drop reduction, although sensible, is nevertheless limited and is always such that the pressure drops progressively increase as the production capacity increases.

An object of the present invention is to provide a reactor for conducting catalyzed exothermic reactions that eliminates, or at least substantially reduces, the above-mentioned drawbacks.

More particularly, it is an object of this invention to provide a catalytic reactor capable of reducing the pressure drops of the reacting gases, thus allowing one to save compression energy of said gases while retaining the reactor diameter, also with high production capacities such as, e.g., 5,000 t/d of ammonia, within reasonable limits acceptable to both manufacturers and forwarders.

Another object of the present invention is to provide a catalytic reactor in which the distribution of the reacting gases in the catalytic mass does not cause any difficulty, thus avoiding the necessity of adopting any particular device or arrangement for the effective distribution of the reacting gases.

Still another object of this invention is to provide a multilayer catalyst reactor without the necessity of employing a plurality of devices for the intermediate cooling of the reacting gases between each catalyst layer and the successive one, said intermediate cooling being easily achieved by heat removal with the generation of water vapor in a boiler.

These and still other objects will become more clearly apparent from the detailed description given hereinafter and, briefly speaking, are advantageously attained by a reactor for catalyzed exothermic reactions having at least one catalyst layer, said reactor having, according to this invention, each individual catalyst layer arranged between two coaxial cylindrical shells, at least two inlets for the reacting gases to the catalyst being provided in one of said shells and at least two outlets in the other shell.

Figure 2:
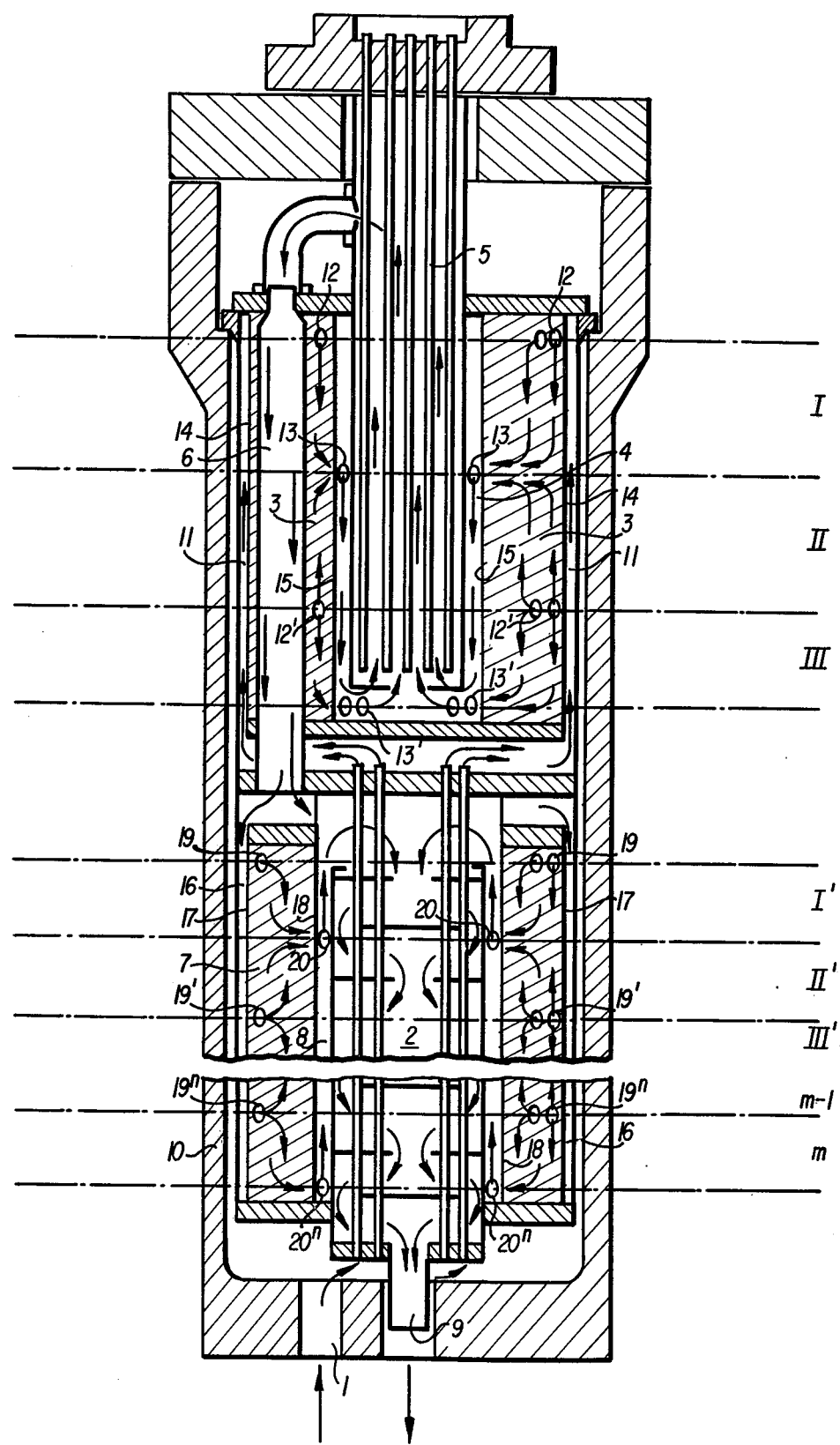

The present invention will be now described in still greater detail with reference to the attached drawings which are provided merely for illustrative purposes and in which:

FIG. 1 shows in schematic form a catalyst layer of a catalytic reactor according to one embodiment of the present invention; and FIG. 2 represents, also in schematic form, a two-layer catalyst reactor according to another embodiment of the present invention.

Referring to FIG. 1, catalyst layer 1 constituting a part of a catalytic reactor for exothermic reactions is arranged in the space delimited by the two coaxial cylindrical shells 2 and 3 and by the two plates 4 and 5. 6 indicates the outer cylindrical shell, coaxial with both shells 2 and 3, and delimiting, along with shell 2, a hollow space 7.

Three sets of openings 8, 8' and 8" are provided in external cylindrical shell 2, such openings representing three inlets to catalyst 1 for the reacting gases that come from the top, flowing in hollow space 7, as indicated in the figure by arrows 9.

Each of inlets 8, 8' and 8" consists of a plurality of openings made in cylindrical shell 2 and aligned on three circumferences that represent the intersections of cylindrical shell 2 with three planes perpendicular to the axis a—a of said cylindrical shell. These planes are indicated by reference numerals A, B and C.

These planes, and in consequence the three sets of inlets 8, 8' and 8", are equispaced from one another in the direction of axis a—a of the cylindrical shell 2. If this equidistance is indicated by d, as shown in FIG. 1, the distance of planes A and C respectively from the two planes D and E (corresponding to the upper end 4 and the lower end 5 of the cylindrical shell 2) is equal to ½d.

In the internal cylindrical shell 3 are four sets of openings 10, 10', 10" and 10'" constituting four outlets from catalyst 1 for the reacted gases flowing through catalytic layer 1, as indicated in FIG. 1 by the arrows 9'. The reacted gases, upon leaving via the four sets of outlets 10, 10', 10" and 10'", enter the cylindrical conduit 11 defined by the internal cylindrical shell 3, and flow downwardly as shown in FIG. 1 by the arrows 9".

Each of the sets of outlets 10, 10', 10" and 10'" consists of a plurality of openings made in the cylindrical shell 3 and aligned on four circumferences that are the intersections of the cylindrical shell 3 with four planes perpendicular to the axis a—a of said cylindrical surface. These planes are indicated by D, F, G and E.

These planes, and in consequence the four outlets 10, 10', 10" and 10'", are equispaced from one another in the direction of axis a—a of the cylindrical shell 3, by a distance d equal to the distance between planes A, B and C.

With this arrangement, each set of inlets 8, 8' and 8" in the direction of axis a—a of the catalytic reactor is located in a median position, i.e., equidistant, with respect to the adjacent sets of outlets indicated by 10 and 10', 10' and 10", 10" and 10'", respectively.

Analogously, each set of outlets 10' and 10" in the direction of axis a—a of the catalytic reactor is located in a median position, i.e. equidistant, with respect to the adjacent sets of inlets indicated by 8 and 8', 8' and 8", respectively.

Catalyst layer 1 is therefore divided by ideal planes D, A, F, B, G, C and E equidistant from one another and containing, alternately, an outlet and an inlet, into six identical zones (indicated in FIG. 1 by I to VI), each having a height equal to ½d. This height ½d is generally between 1000 and 4000 mm. This height therefore corresponds to the distance between two contiguous ideal planes, one of which contains an inlet and the other an outlet.

In each of such zones, or "oduls", the reacting gases—as indicated in FIG. 1 by the arrows 9'"—flow through the catalyst in an axial direction and, what is of great importance for the purpose of obtaining good distribution, under the same dynamic flow conditions.

In fact, the equality of "modules" I to VI obtained through the described positioning of the inlets and the outlets and a suitable dimensioning of each "module" permit one to achieve a good distribution of the reacting gases in and throughout the catalyst mass, so that the reacting gases flow through equal amounts of catalyst at substantially equal flowrates.

Once the flow parameters of the reacting gases, such as e.g. the flowrate, are fixed, and once the diameter of the cylindrical shells 2 and 3, as well as the catalyst volume, granulometry or porosity, are fixed, then it becomes possible to cause the pressure drop to vary and to be lowered, independently of the above-said parameters, this being obtained by varying the dimensions of the "module" and the number of "modules".

It is therefore readily possible to maintain the pressure drops through the catalyst within predetermined limits, independently of the production capacity of the catalytic reactor.

For instance, in the case of a catalyst layer employed in a catalytic reactor for ammonia synthesis, the flow parameters are as follows:

820,000 $Nm^3/h$ of a synthesis gas having a density of 0.47 $kg/Nm^3$, at a pressure of 230 $kg/cm^2$ and at a mean temperature of 470° C., shall flow through a catalyst mass having a volume of about 21 $m^3$ and an average granulometry of 2 mm. The catalyst is arranged between two coaxial cylindrical shells, of which the external one has an inside diameter of 1850 mm and the internal one has an outside diameter of 1000 mm. The total height of the catalyst layer is about 11,000 mm. By providing the external shell with three sets of inlets and the internal shell with three sets of outlets according to the modalities already described, the catalyst layer is divided into five "modules" lying one above the other, through which the reacting gas flows in parallel, and in axial direction, through each of them, eacch of these "modules" having a height of 2200 mm, corresponding to the height indicated above as ½d.

With this arrangement, the pressure drops that the catalyst layer opposes to the reacting gas flow amount to 1.35 $kg/cm^2$, i.e. a value low enough to limit the consumption of energy required for the reacting gas circulation, and yet high enough to insure good distribution of the reacting gas in and through the catalyst, without requiring the adoption of special distributing devices which are expensive and require much space.

If, with the same flow parameters, a simple axial flow should be employed, i.e. if all the reacting gas were to be conveyed through the whole catalyst layer by letting it all flow in an axial direction from one end of the layer, for example from the upper end to the opposite end, then the pressure drops would be equal to 143.7 $kg/cm^2$, which is an absolutely impermissible value for the mechanical resistance of the catalyst that would be reduced to powder, as well as for the very high energy consumption required for the gas circulation.

In the case of the above-cited example, the distance indicated by d in FIG. 1 is equal to 4400 mm, while the distance between the two cylindrical shells containing the catalyst is equal to 425 mm, wherefore the gas flow in each catalyst "module" can be assumed to be substantially axial and to have a constant flow distribution that prevents the forming of preferential or uneven passages through the catalyst mass.

By varying the flow parameters, the dimensions of the catalyst "modules" and/or the number of same can be varied as desired. In general, the distance between two adjacent sets of inlets to the catalyst mass or between two adjacent sets of outlets, that is to say d in FIG. 1, is between 2000 and 8000 mm.

As shown in FIG. 1, the reacting gases flowing out from each of "modules" I to VI of catalyst layer 1, are collected, as already explained, in cylindrical conduit 11 to form a sole flow 9", that flows downwardly and, after cooling, passes to a subsequent catalyst layer, not represented in the drawing. The fact of having a sole flow 9' simplifies the modalities for obtaining an intermediate cooling of the reacting gases between two successive catalyst layers, and permits one to effect such cooling between the various catalyst layers by means of one operation only, e.g. by injection of gas at a lower temperature than the reacting gases, or, especially in the case of highly exothermic reactions such as, for instance, the per se known ammonia or methanol synthesis, by providing in the catalytic reactor interior a boiler that generates high pressure water vapor, thus recovering most of the reaction heat at the highest thermodynamic level, according to the method described in Italian Pat. No. 792,444 of Montecatini Edison S.p.A.

If the catalytic reactor consists of a single catalyst layer 1, the hot reacted gases, collected in cylindrical conduit 11 to form a single flow 9", are cooled in a heat exchanger that preheats the incoming reacting gases 9, and then leave the reactor.

FIG. 2 shows another catalytic reactor arrangement, particularly suited to the ammonia or methanol synthesis, of the type having two adiabatic catalyst layers lying one over the other, according to the present invention, and with intermediate cooling of the reacting gases between said two catalyst layers by the provision of a boiler for the generation of high pressure steam.

According to FIG. 2, the reacting gases enter the reactor through inlet opening 1 existing in a pressure vessel 10 forming the cylindrical shell of the catalytic reactor.

The reacting gases are pre-heated in a centrally-disposed heat exchanger 2, through which they flow in the tube side, up to the reaction temperature by exchanging heat with the reacted gas leaving the catalytic reactor via outlet opening 9.

Heat exchanger 2 is arranged coaxially with respect to cylindrical shells 17 and 18 of the lower catalyst layer 7, and inside the internal cylindrical shell 18.

At the outlet of heat exchanger 2, the reacting gases, via the hollow space 11, flow through the first upper catalyst layer 3. The catalyst layer 3 is composed and arranged similarly to catalyst layer 1, described above with reference to FIG. 1, and is contained in coaxial cylindrical shells 14 and 15.

Sets of gas inlets 12 and 12' to catalyst layer 3 and sets of outlets 13 and 13', shaped and arranged as described above for FIG. 1, divide this first catalyst layer 3 into three "modules", indicated in FIG. 2 by I, II and III.

The reacting gases at the outlet of the upper catalyst layer 3 collect in annular conduit 4, defined by the internal cylindrical shell 15 and the outside surface of steam-generating boiler 5, from which they flow through boiler 5 and are cooled down.

As specified hereinbefore, such boiler 5 is the only cooling device for the reacting gases durng their flow from the first upper layer 3 of catalyst to the second lower layer, the boiler 5 being arranged coaxially with respect to cylindrical shells 14 and 15 and inside the internal cylindrical shell 15.

The reacting gases flow out from boiler 5 and are conveyed by means of conduit 6 and hollow space 16 to a lower catalyst layer 7.

Catalyst layer 7 is composed and arranged analogously to catalyst layer 1 described above with reference to FIG. 1, and is contained in coaxial cylindrical shells 17 and 18.

The $n+1$ sets of inlets 19, 19', ... $19^n$ for the admission of the reacting gases to catalyst layer 7, and the $n+1$ sets of outlets 20 ... $20^n$, shaped and arranged in analogy with the description referred to above in FIG. 1, divide this second catalyst layer 7 into m "modules", indicated in the figure by I', II', III', ... m−1, and m.

At the outlet of catalyst layer 7 the reacted gases collect in annular conduit 8, defined by the internal cylindrical shell 18 and the outside surface of heat exchanger 2, from which they pass through exchanger 2, in the jacket side, where they are cooled down in countercurrent to the gases entering from inlet opening 1, thereupon flowing out from the discharge outlet 9 of the catalytic reactor.

The reacting gases flowing from the first to the second catalyst layer can be cooled down, instead of by means of boiler 5, by the injection of cooler fresh gases coming from the outside. In such case conduit 6 permits one to obtain a thorough mixing of said gases.

In the event the lower catalyst layer 7 should be lacking, the reacted gases leaving boiler 5 is then directly conveyed to the exchanger 2.

The advantages offered by the present invention clearly appear from the description given above, and they may be summarized as follows:

The catalytic reactor according to the present invention permits one to attain a good distribution of the reacting gases in and throughout the catalyst mass without requiring the adoption of special distributing devices that are expensive and require much space; it permits one to operate with low pressure drops which in turn permit a catalytic reactor diameter that falls within limits acceptable in practice, while at the same time attaining high production capacities (e.g. 5000 t/d of ammonia); it permits one to recover the reaction heat at the maximum or optimum thermodynamic level, since it thus becomes feasible to employ a boiler that provides an inter-layer cooling effect with the generation of high pressure steam.

The sets of inlets to and outlets from the catalyst layers have been described above as being disposed in equispaced planes for the purpose of insuring the uniform or substantially uniform distribution of the flowing gases into, through, and from the catalyst. For the same reason, the inlets and outlets constituting the sets of inlets and outlets at each level or plane of the catalytic reactor are preferably evenly or substantially evenly spaced around the circumference of the cylindrical shell(s).

What is claimed is:

1. A catalytic reactor for catalyzed exothermic reactions having two catalyst layers, lying one over the other, wherein each of said two catalyst layers is contained within two coaxial cylindrical shells, said shells being provided with inlets to and outlets from said catalyst layer for reacting gases, each of said inlets and outlets consisting essentially of a plurality of openings in said cylindrical shells aligned on circumferences of said cylindrical shells defined by the intersections of said cylindrical shells with planes equispaced from one another and perpendicular with respect to the axis of said cylindrical shells, wherein the distance between two of said equispaced and perpendicular planes, one of which defines an inlet and the other an adjacent outlet, is between 1000 and 4000 mm, and at least one of said inlets is in a median position with respect to an adjacent pair of outlets, and the portion of catalyst layer bounded by the planes of said adjacent outlets defines a catalyst zone through which the reacting gases flow substantially in axial and opposite directions, said reactor is provided with a heat exchanger means arranged coaxially with respect to the two cylindrical shells defining the lower catalyst layer and positioned inside the internal cylindrical shell thereof, said reactor is provided with a boiler means for steam generation arranged coaxially with respect to the two cylindrical shells of the upper catalyst layer and positioned inside the internal cylindrical shell thereof, and reaction gas feed means communicating with said heat exchanger means such that reacting gases fed to the reactor are pre-heated in said heat exchanger, passed through said upper catalyst layer, cooled in said boiler, passed through said lower catalyst layer, and finally cooled in said heat exchanger.

* * * * *